(12) United States Patent
Molenberg

(10) Patent No.: US 7,741,427 B2
(45) Date of Patent: *Jun. 22, 2010

(54) BARRIER MEMBRANE

(75) Inventor: Aaldert Rens Molenberg, Binningen (CH)

(73) Assignee: Straumann Holding AG, Basel (CH)

( * ) Notice: Subject to any disclaimer, the term of this patent is extended or adjusted under 35 U.S.C. 154(b) by 636 days.

This patent is subject to a terminal disclaimer.

(21) Appl. No.: 11/629,567

(22) PCT Filed: May 9, 2005

(86) PCT No.: PCT/EP2005/004977

§ 371 (c)(1),
(2), (4) Date: Dec. 14, 2006

(87) PCT Pub. No.: WO2005/123156

PCT Pub. Date: Dec. 29, 2005

(65) Prior Publication Data

US 2008/0039577 A1 Feb. 14, 2008

(30) Foreign Application Priority Data

Jun. 16, 2004 (EP) .................................. 04104072

(51) Int. Cl.
*C08G 67/02* (2006.01)
(52) U.S. Cl. ..................... 528/392; 524/547; 524/558; 525/326.8; 525/326.9; 525/329.4; 525/329.5; 526/318; 560/198; 568/62
(58) Field of Classification Search .................. 528/392
See application file for complete search history.

(56) References Cited

U.S. PATENT DOCUMENTS

| 3,989,740 | A | * | 11/1976 | Broussard et al. ........... 560/224 |
|---|---|---|---|---|
| 4,021,310 | A | | 5/1977 | Shimizu et al. |
| 4,804,891 | A | | 2/1989 | Sweeney |
| 4,894,238 | A | | 1/1990 | Embry |
| 5,368,859 | A | | 11/1994 | Dunn et al. |
| 5,410,016 | A | | 4/1995 | Hubbell |
| 5,874,500 | A | | 2/1999 | Rhee |

(Continued)

FOREIGN PATENT DOCUMENTS

DE 215 699 A1 11/1984

(Continued)

OTHER PUBLICATIONS

Shearwater product catalog, year 2000.*

(Continued)

*Primary Examiner*—Randy Gulakowski
*Assistant Examiner*—Shane Fang
(74) *Attorney, Agent, or Firm*—Rissman Hendricks & Oliverio LLP

(57) ABSTRACT

The present invention relates to a cell-occlusive membrane, obtainable by reaction of at least two precursors in the presence of water. The first precursor A comprises a core and n chains each having a conjugated unsaturated group or a conjugated unsaturated bond, and the second precursor B comprises a core and m chains each having a thiol group, wherein m is greater than or equal to 2, n is greater than or equal to 2, and m+n is greater than or equal 5. The reaction forms a three dimensional network with crosslinking-points. The adjacent crosslinking-points are connected by a chain having less than 600 atoms.

5 Claims, 2 Drawing Sheets

U.S. PATENT DOCUMENTS

Figure 1:
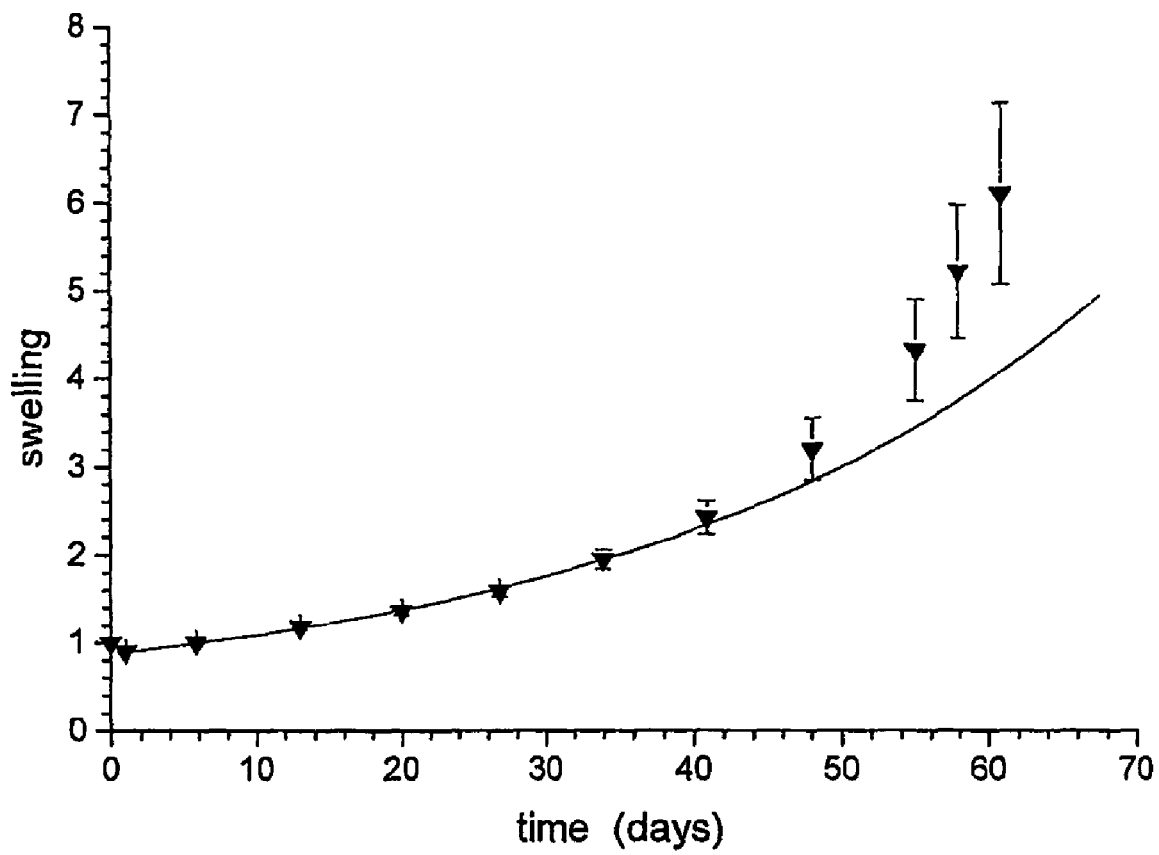

| | | | |
|---|---|---|---|
| 6,051,648 A | 4/2000 | Rhee et al. | |
| 6,258,351 B1 | 7/2001 | Harris | |
| 6,432,397 B1 | 8/2002 | Harris | |
| 6,558,658 B2 | 5/2003 | Harris | |
| 6,624,245 B2 | 9/2003 | Wallace et al. | |
| 7,009,034 B2 | 3/2006 | Pathak | |
| 2003/0220245 A1* | 11/2003 | Hubbell et al. | 514/12 |

FOREIGN PATENT DOCUMENTS

| | | |
|---|---|---|
| EP | 0 334 500 A1 | 9/1989 |
| EP | 0367362 B1 | 6/1994 |
| EP | 1080700 A | 3/2001 |
| EP | 0705298 B1 | 3/2002 |
| EP | 1053019 B1 | 12/2003 |
| EP | 1411075 A2 | 4/2004 |
| EP | 1061954 B1 | 6/2004 |
| EP | 0876165 B1 | 6/2006 |
| GB | 942318 | 11/1963 |
| JP | 56084708 | 7/1981 |
| JP | 08155024 | 6/1996 |
| RO | 81794 | 5/1983 |
| WO | WO 92/10218 A | 6/1992 |
| WO | WO 94/03155 A1 | 2/1994 |
| WO | WO 97/22371 A1 | 6/1997 |
| WO | WO 98/12274 A1 | 3/1998 |
| WO | WO 99/14259 A1 | 3/1999 |
| WO | WO 00/33764 A1 | 6/2000 |
| WO | WO 00/44808 A1 | 8/2000 |
| WO | WO 00/59559 A1 | 10/2000 |
| WO | WO 01/16210 A1 | 3/2001 |
| WO | WO 01/92584 A1 | 12/2001 |
| WO | WO 02/102864 A1 | 12/2002 |
| WO | WO 03/080144 A1 | 2/2003 |
| WO | WO 03/040235 A1 | 5/2003 |
| WO | WO 03/080144 A | 10/2003 |
| WO | WO 2005/018491 A2 | 3/2005 |

OTHER PUBLICATIONS

Elbert et al., Protein Delivery from Materials Formed by Self-Selective Conjugate Addition Reactions, Journal of Controlled Release, 76, 2001, p. 11-25.

Shearwater Corporation Catalog 2001, Polyethylene Glycol and Derivatives for Biomedical Applications.

International Search Report mailed Aug. 31, 2005 from International Application No. PCT/EP2005/004977.

U.S. Appl. No. 60/110,849, Pathak (provisional application).

U.S. Appl. No. 60/040,417, Pathak (provisional application).

U.S. Appl. No. 60/039,904, Pathak (provisional application).

U.S. Appl. No. 60/026,526, Pathak (provisional application).

European Search Report and Annex (Office Action) in corresponding EP 0502 0181 dated Feb. 7, 2006.

Levy, L., Inhibition of Acrylic Acid Polymerization by Phenothiazine and p-Methoxyphenol. II. Catalytic Inhibition by Phenothiazine, Journal of Polymer Science Part A: Polymer Chemistry, 1992, 569-576, vol. 30, John Wiley & Sons, Inc. U.S.A.

Mitchell, S.C., The Toxicity of Phenothiazine, Drug Metabolism and Drug Interactions, 1994, 201-235, vol. 11, No. 3, Freund Publishing House Ltd., U.K.

MacChiarini, P. et al., "Experimental and Clinical Evaluation of a New Synthetic, Absorbably Sealant to Reduce Air Leaks in Thoracic Operations," Journal of Thoracic and Cardiovascular Surgery, Apr. 1999, 751-758, Mosby Inc.

Ranger, W. et al., "Pneumostasis of Experimental Air Leaks with a New Photopolymerized Synthetic Tissue Sealant," The American Surgeon, Sep. 1997, 788-795.

Lutzi, F.G. et al., "Tinted Hydrogel Lenses Permanancy of Tint," Am J Optom & Physiol Optics, May 1985, 329-333, vol. 62, No. 5, American Academy of Optometry, USA.

Schulze and Vogel, Aspects of the Safe Storage of Acrylic Monomers: Kinetics of the Oxygen Consumption, Chem. Eng. Technol., 1998, 829-837, vol. 21, No. 10, Wiley-VCH, DE.

* cited by examiner

BARRIER MEMBRANE

FIELD OF THE INVENTION

The present invention relates to a cell-occlusive membrane, which is obtainable by reaction of at least two precursors in the presence of water and a method for preparing the membrane.

BACKGROUND

Implants that are used for insertion into bone, for example titanium screws to be placed into the jaw for attachment of artificial teeth are known per se. The function of such an implant can be hampered by an insufficient bone volume or the presence of bone defects at the site of implantation. An often applied measure to promote bone formation at the implantation site is Guided Bone Regeneration (GBR). In this procedure, the site where bone formation is desired is separated from the surrounding soft tissue by a barrier membrane that inhibits non-osteogenic soft tissue cells from entering the site, thus allowing cells from the bone marrow to fill it with bone. Additionally, an osteoconductive bone filling material can be used to support the membrane.

There are several types of cell-occlusive membranes that are used in the field of guided bone regeneration or tissue regeneration in general. Commercially available cell-occlusive membranes can be grouped according to their origin into xenogenic membrane material derived from individuals of different species and synthetically manufactured membrane material.

Xenogenic material always bears the risk of infection. Most membrane materials are sold in sheets and need to be cut to size by the surgeon, which is time consuming. Further this procedure results in difficulties due to shape matching. An example for a xenogenic material is collagen, which is biodegradable and hydrophilic.

An example for synthetic material is PTFE (Teflon). The PTFE membrane is hydrophobic and therefore does not attach well to biological tissue and often has to be attached using pins or screws. Furthermore the material is not biodegradable and thus has to be removed after the healing process in a second invasive procedure.

Biodegradable materials are known in the art. In WO 01/92584 a matrix material is disclosed which is formed by nucleophilic addition reaction to conjugated unsaturated groups. A pharmaceutically active component is covalently attached to the biomaterial, which will be subsequently released into the body. The biodegradable material degrades under physiological conditions within one month.

WO 00/44808 also discloses a polymeric biomaterial formed by nucleophilic addition reactions to conjugated unsaturated groups. The obtained hydrogels may be used for example as glues or sealants and as scaffolds for tissue engineering and wound healing applications. Also said hydrogels degrade fast under physiological conditions.

U.S. Pat. No. 5,874,500 discloses a crosslinked polymeric composition comprising a first synthetic polymer containing two or more amino groups covalently bound to a second synthetic polymer containing multiple electrophilic groups and a biologically active component. Said composition may be used to effect adhesion between a first surface and a second surface, to effect tissue augmentation, to prevent the formation of surgical adhesion and to coat a surface of a synthetic implant.

SUMMARY OF THE INVENTION

As used herein, the words "polymerization" and "cross-linking" are used to indicate the linking of different precursors to each other to result in a substantial increase in molecular weight. "Cross-linking" further indicates branching, typically to yield a polymer network.

By "self selective" is meant that a first precursor A of the reaction reacts much faster with a second precursor B than with other compounds present in the mixture at the site of the reaction, and the second precursor B reacts much faster with the first precursor A than with other compounds present in the mixture at the site of the reaction. The mixture may contain other biological materials, for example, drugs, peptides, proteins, DNA, cells, cell aggregates and tissues.

By "conjugated unsaturated bond" the alternation of carbon-carbon, carbon-heteroatom or heteroatom-heteroatom multiple bonds with single bonds. Such bonds can undergo addition reactions.

By "conjugated unsaturated group" a molecule or a region of a molecule, containing an alternation of carbon-carbon, carbon-heteroatom or heteroatom-heteroatom multiple bonds with single bonds, which has a multiple bond which can undergo addition reactions is meant. Examples of conjugated unsaturated groups include, but are not limited to acrylates, acrylamides, quinines, and vinylpyridiniums, for example 2- or 4-vinylpyridinium.

The problem of the present invention is to provide a biodegradable membrane which prevents surrounding soft tissue from interaction with the region to be protected, which does not bear the risk of infection.

The problem is solved by a cell-occlusive membrane formed by reaction of at least two precursors in the presence of water, wherein a first precursor A comprising a core carrying n chains each having a conjugated unsaturated group or a conjugated unsaturated bond attached to any of the last 20 atoms of the chain and a second precursor B comprising a core carrying m chains each having a thiol group attached to any of the last 20 atoms of the chain, wherein m is greater than or equal to 2, n is greater than or equal to 2, m+n is greater than or equal to 5, the first precursor A and the second precursor B forming a three dimensional network with crosslinking-points, wherein each core of the precursors forms a crosslinking-point if m and n are greater than 2, and if m is equal to 2 the corresponding crosslinking-point corresponds to the core of the adjacent first precursor A, and if n is equal to 2 the crosslinking-point corresponds to the core of the adjacent second precursor B, and the adjacent crosslinking-points are connected by a chain having less than 600 atoms.

The membrane according to the present invention is obtainable by reaction of two or more precursors. Due to the combination of the characteristics of the precursors, that means the number of chains of the precursors as well as fact that the adjacent crosslinking-points are connected by a chain having less than 600 atoms, the resulting membrane is cell-occlusive. The membrane according to the present invention prevents the surrounding soft tissue from interaction with the region to be protected. This allows a fast bone regeneration in a bone defect.

Due to the fact that the membrane is of non-animal origin, the risk of inflammation and transmission of animal pathogens is reduced. Further, the membrane is bio-degradable, which avoids a second surgery. However it is stable enough to ensure a maintenance of the barrier function during complete healing time for an effective bone regeneration in implant bed defects, which means that there is a predictable treatment outcome which is important to the surgeon. The membrane is degradable within about 6 months. The degradation products are easily excreted and non-toxic.

The membrane according to the present invention may be applied in situ which means that a fast application is possible, which is required by the surgeon and the patient. Due to the mode of application the membrane will take the shape of the underlying surface, thus ensuring optimum fit and hold. No fixation of such a membrane is necessary. That means it is easy to handle since an extra-oral tailoring is avoided. Because of the perfect fit there is a significantly lower risk of undesired granule migration.

The first precursor A comprises a core which carries n chains with a conjugated unsaturated group or a conjugated unsaturated bond attached to any of the last 20 atoms of the chain. In a preferred embodiment said conjugated unsaturated group or conjugated unsaturated bond is terminal. The core can be a single atom such as a carbon or a nitrogen atom or small molecules such as an ethylene oxide unit, a sugar, a multifunctional alcohol, such as pentaerythritol, glycerine or oligoglycerine, such as hexaglycerol. The chains are linear polymers or linear or branched alkyl chains optionally comprising heteroatoms, amide groups or ester groups. Beside the chains the core may be additionally substituted with linear or branched alkyl residues or polymers which have no conjugated unsaturated groups or bonds. In a preferred embodiment the first precursor A has 2 to 10 chains, most preferably 4 to 8 chains. The conjugated unsaturated bonds are preferably acrylates, acrylamides, quinines, 2- or 4-vinylpyridiniums, and itaconate esters of formula Ia or Ib

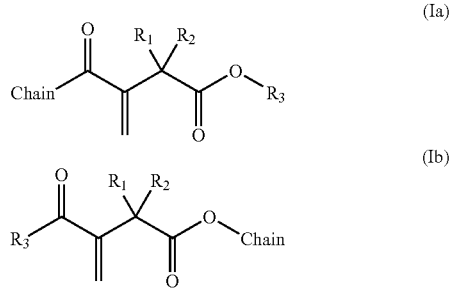

wherein $R_1$ and $R_2$ are independently hydrogen, methyl, ethyl, propyl or butyl, and $R_3$ is a linear or branched C1 to C10 hydrocarbon chain, preferably methyl, ethyl, propyl or butyl.

The second precursor B comprising a core carrying m chains each having a thiol group attached to any of the last 20 atoms at the end of the chain. For example a cysteine residue may be incorporated into the chain. Preferably the thiol group is terminal. The core can be a single atom such as a carbon or a nitrogen atom or small molecules such as an ethylene oxide unit, a sugar, a multifunctional alcohol, such as pentaerythritol, glycerine or oligoglycerine, such as hexaglycerol. The chains are linear polymers or linear or branched alkyl chains optionally comprising heteroatoms, esters groups or amide groups. In a preferred embodiment the second precursor B has 2 to 10 chains, most preferably 4 to 8 chains.

The first precursor A compound has n chains, whereby n is greater than or equal to 2, and the second precursor B compound has m chains, whereby m is greater than or equal to 2. The first and/or the second precursor may comprise further chains which are not functionalized. The sum of the chains of the first and the second precursors, that means m+n, is greater than or equal 5. Preferably the sum of m+n is equal or greater than 8 to obtain a dense three-dimensional network.

Each core of the precursors forms a crosslinking-point if m and n are both greater than 2. If m is equal 2, that means if the second precursor B is linear, the corresponding crosslinking-point corresponds to the core of the adjacent first precursor A. If n is equal 2, that means if the first precursor A is linear, the crosslinking-point corresponds to the core of the adjacent second precursor B. The adjacent crosslinking-points are connected by a chain having less than 600 atoms. Said 600 atoms are only the atoms which are in the backbone of the chain, that means not counting substituents or H atoms.

Preferably the number of atoms between the two adjacent crosslinking-points is smaller than about 330 . . . atoms, most preferably between 30 and 120 atoms. Therefore the meshes of the resulting three-dimensional network are several orders of magnitude smaller than the dimensions of a cell (the dimension of a cell is 1 to 100 μm), which results in a cell-occlusive membrane.

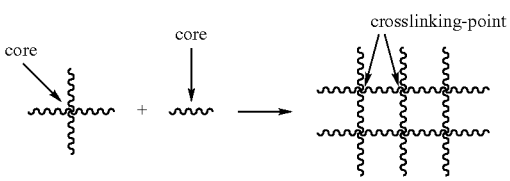

Since the number of chains of the first and the second precursors (n+m) is at least 5 and the distances between the core of the first precursor A and the core of the second precursor B is small, the water content in the network is reduced which results in a longer in vivo stability. But the presence of water ensures the transport of small molecules, that means that waste material can be transported away from the cells and nutrient can enter into the cells.

The reaction of the first and the second precursors is preferably based on the base catalyzed Michael type addition between the conjugated unsaturated group or the conjugated unsaturated bond of the first precursor A and the thiol group of the second precursor B:

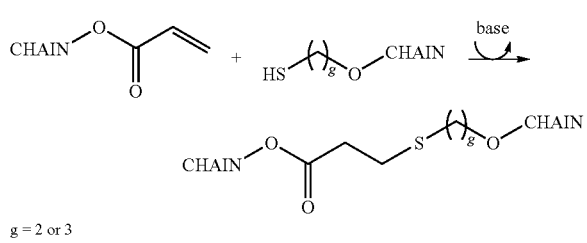

g = 2 or 3

The resulting linkage is hydrolyzed in contact with water. The rate of the hydrolysis reaction depends on the temperature and the value of the pH, which is 7.4 in most tissues. After hydrolysis of several bonds the cross-linked network degrades or breaks down because of hydrolysis of the unstable linkages.

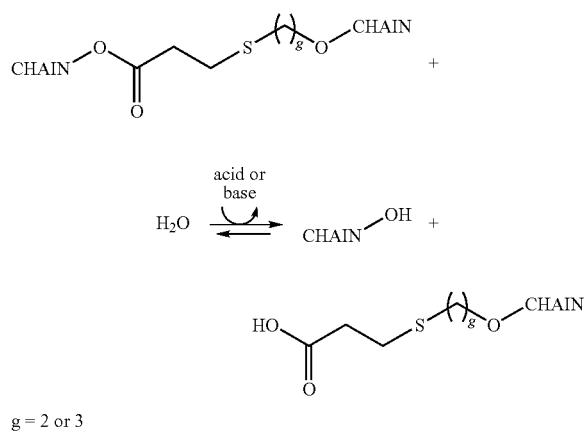

g = 2 or 3

In a preferred embodiment the chains of the first precursor A and/or the chains of the second precursor B are linear polymers. Said polymers are preferably selected from the group consisting of poly(ethylene glycol), poly(ethylene oxide), poly(vinyl alcohol), poly(ethylene-co-vinyl alcohol), poly(acrylic acid), poly(ethylene-co-vinyl-pyrrolidone), poly(ethyloxazoline), poly(vinyl pyrrolidone), poly(ethylene-co-vinyl pyrrolidone), poly(maleic acid), poly(ethylene-co-maleic acid), poly(acrylamide) or poly(ethylene oxide)-co-polypropylene oxide) block copolymers. Said polymers can also be copolymers, block copolymers, graft copolymers, or random copolymers. Blocks, which are polymerized on the ends of the hydrophilic polymers, can be composed of, for example, lactic acid, glycolic acid, ε-caprolactone, lactic-co-glycolic acid oligomers, trimethylene carbonate, anhydrides, and amino acids.

In a preferred embodiment the chains of the precursor molecules are poly (ethylene glycole) molecules (PEG). PEG is highly water soluble, available in high quality and many different structures. Further it is non-toxic and FDA approved for oral and topical administration and injections to humans.

In a most preferred embodiment the first precursor A is a PEG-acrylate with 8 chains and an approximate molecular weight of 2 k (kg/mol=kDa). The molecular weight may vary by ca. ±20% and thus the values for v are only approximate values.

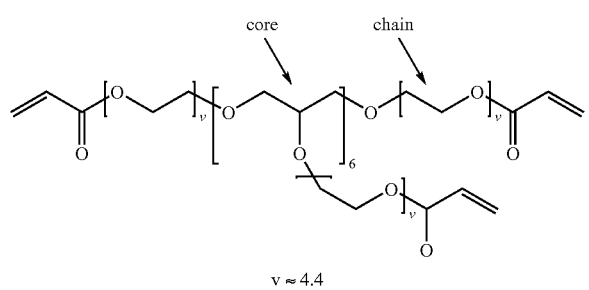

v ≈ 4.4

The second precursor B is a PEG-thiol with four chains and an approximate molecular weight of 2 k (kg/mol=kDa).

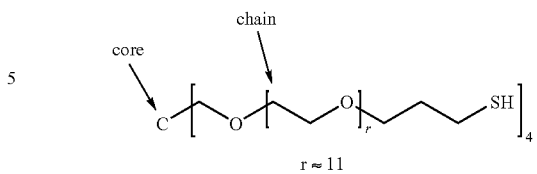

r ≈ 11

In a further embodiment of the present invention a viscosity modifying agent may be added to the precursors in order to prevent the liquid from running away before it has gelled. Possible viscosity modifying agents are for example CMC or xanthan.

In a further preferred embodiment a stabilizer may be added to avoid self-polymerization of the first precursor A. A possible stabilizer is methylene blue which ensures a good stabilization.

To obtain the membrane according to the present invention the precursors are mixed together in the presence of water, preferably water buffered at physiologic or nearly physiological pH. It is not necessary that the monomers are entirely soluble in water. In general the cross-linking is completed within a relatively short period of time (i.e. 10 seconds to 15 minutes). Therefore the surgical site may be closed relatively soon upon completion of the surgical procedure.

Mixing to form the membrane according to the present invention can occur by several means. In a preferred embodiment the first precursor A is mixed with a first buffer and the second precursor B is mixed with a second buffer. Upon application the two mixtures are mixed further by means of a static mixer attached to two syringes and the resulting mixture is applied in situ.

The mixing can also occur between fine droplets of each of the two precursor solutions in an air spray. One solution could be prepared from both precursors, but at a pH, for example, such that the reaction can not proceed or proceeds only slowly. After placement of the pre-mixed precursor solution, pH could be adjusted, for example by mixing with an acid or a base, or by a chemical reaction to create an acid or base, or diffusion of an acid or base, to result in a final condition in the final precursor solution that is appropriate for the chemical reaction to proceed. Another approach can be to prepare the final precursor solution at a temperature such that the reaction can not proceed or proceeds only very slowly, either related to the activation energy of the reaction or to a buffer with temperature-sensitive characteristics or both. Upon warming or cooling (most usefully warming) to the final application temperature (e.g., to body temperature after injection), the conditions in the final precursor solution would be appropriate for the chemical reaction to proceed.

The first and the second precursors may be sold independently from each other. In a preferred embodiment they are sold together in form of a kit comprising the first precursor A and the second precursor B, wherein said precursors are separated from each other. This can for example be done by two syringes, a container with two compartments, or two different containers. Said kit may comprise additionally a buffered aqueous solution. It is also possible that the buffered solution is separated from the first precursor A and the second precursor B.

EXAMPLES

Example 1

PEG-tetrathiol 2 k

A.) PEG-tetraallylether 2 k

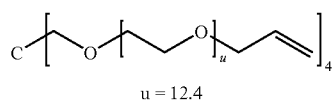

u = 12.4

20.3 g of 4-arm PEG 2 k ($M_n$=2323 g/mol, 35.7 meq OH) were dissolved in 200 ml of dry tetrahydrofuran under an Ar atmosphere. The solution was dried by refluxing the solvent over molecular sieves until the water content had fallen below 200 ppm. Then, it was allowed to cool down to room temperature and 2.69 g of a 60% NaH suspension in mineral oil (67 mmol) were added and allowed to react for 15 min, after which 8.75 g of allylbromide (73.3 mmol) were added. The suspension was brought to reflux and stirred overnight. After cooling down, it was filtered through ca. 1 cm of Celite 545, yielding a pale yellow, clear solution. Solvent and excess allylbromide were removed by rotary evaporation and the remaining oil was redissolved in 200 ml of water. Washing the resulting emulsion with three 50 ml portions of diethyl ether yielded a clear, pale yellow solution in which 20 g of NaCl were dissolved. The product was extracted with three 50 ml portions of dichloromethane and the combined organic layers were dried with $MgSO_4$ and filtered. Removing the solvent by rotary evaporation yielded 21.3 g (98%) of a pale yellow oil. $^1H$ NMR confirmed the structure of the product.

B.) PEG-tetra(thioacetate) 2 k

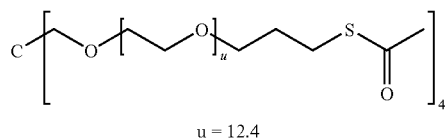

u = 12.4

19.7 g of PEG-tetraallylether 2 k ($M_n$=2483 g/mol, 31.7 meq allyl) and 1.70 g (10.4 mmol) of AIBN were dissolved in 150 ml of stabilizer-free tetrahydrofuran and the solution was degassed by four cycles of evacuation and purging with Ar. The solution was brought to reflux and over a period of 20 hrs. three 10 ml portions of a degassed solution of 9.0 ml (135 mmol) of thioacetic acid in 21 ml of tetrahydrofuran were added. Before the last addition, 0.53 g (3.3 mmol) of AIBN were added. After stirring under reflux for another four hours, the product was isolated as described under A.), yielding 22.2 g (100%) of a light yellow oil. The structure of the product and the complete conversion of the allyl groups were confirmed by $^1H$ NMR, which showed a degree of functionalization of ca. 95%.

C.) PEG-tetrathiol 2 k

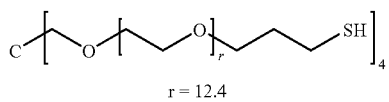

r = 12.4

10.9 g of PEG-tetra(thioacetate) 2 k ($M_n$=2787 g/mol, 15.7 meq thioacetate) were dissolved in 100 ml of water and degassed by four cycles of evacuation and purging with Ar. Then, 100 ml of a degassed 0.4 M aqueous NaOH solution were added, and the resulting solution was degassed again. After stirring for two hours at room temperature, 12.7 ml of a 2.00 M aqueous $KHSO_4$ solution were added, yielding a solution with pH 6.5. The product was isolated as described under A.), but kept under Ar during the process, yielding 10.1 g (98%) of a yellow oil. By IR spectroscopy no carbonyl groups (signal at 1690 $cm^{-1}$) could be detected and $^1H$ NMR confirmed the structure of the product.

Example 2

Linear PEG-dithiol 3.4 k

A.) α,ω-bis allyl-PEG

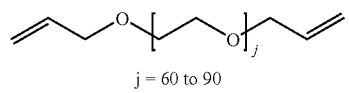

j = 60 to 90

34.0 g of α,ω-bishydroxy-PEG ($M_n$=3391 g/mol, 20.1 meq OH) were dissolved in 250 ml of dry tetrahydrofuran under an Ar atmosphere. The solution was dried by refluxing the solvent over molecular sieves until the water content had fallen below 100 ppm. Then it was allowed to cool down to ca. 50° C. and 1.68 g of a 60% NaH suspension in mineral oil (42 mmol) were added and allowed to react for 15 min, after which 4.0 ml allylbromide (47 mmol) were added. The suspension was brought to reflux and stirred overnight. After cooling down, it was filtered through ca. 1 cm of Celite 545, yielding a pale yellow, clear solution. Solvent and excess allylbromide were removed by rotary evaporation and the resulting solid was redissolved in 200 ml of water. Washing the resulting emulsion with two 50 ml portions of diethyl ether yielded a clear, pale yellow solution in which 20 g of NaCl were dissolved. The product was extracted with three 50 ml portions of chloroform and the combined chloroform layers were dried with $MgSO_4$, filtered and concentrated by rotary evaporation to ca. 80 ml. Precipitation in 1.2 l of cold diethyl ether and subsequent filtration and drying at 60° C. in a vacuum oven yielded 33.3 g (96%) of a white powder. The structure of the product was confirmed by $^1H$ NMR, which showed a degree of functionalization of ca. 97%.

B.) α, ω-bis(3-thioacetylpropyl)-PEG

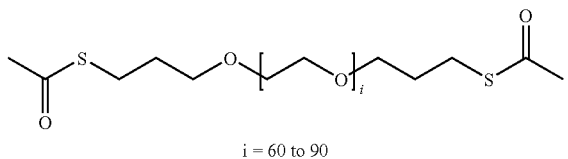

i = 60 to 90

31.7 g of α,ω-bisallyl-PEG ($M_n$=3471 g/mol, 18.3 meq allyl) and 1.02 g (10.4 mmol) of AIBN were dissolved in 200 ml of stabilizer-free tetrahydrofuran and the solution was degassed by four cycles of evacuation and purging with Ar. The solution was brought to reflux and over a period of 21 hrs. Three 10 ml portions of a degassed solution of 5.2 ml (73 mmol) of thioacetic acid in 25 ml of tetrahydrofuran were added. Before the last addition, 0.26 g (1.6 mmol) of AIBN were added. After stirring under reflux for another five hours, the product was isolated as described under A.), yielding 30.8 g (93%) of an almost white powder. The structure of the product and the complete conversion of the allyl groups were confirmed by $^1H$ NMR, which showed a degree of functionalization of ca. 97%.

C.) α,ω-bis(3-mercaptopropyl)-PEG 3.4 k

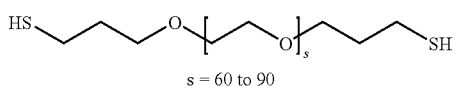

s = 60 to 90

8.5 g of α,ω-bis(3-thioacetylpropyl)-PEG ($M_n$=3623 g/mol, 4.7 meq thioacetate) were dissolved in 70 ml of a degassed 0.20 M aqueous NaOH solution and stirred for two hours at room temperature under Ar. Then, 2.00 M aqueous KHSO$_4$ was added until the solution had pH 6. The product was isolated as described under A.), but kept under Ar during the process, yielding 6.4 g (76%) of a white powder. By IR spectroscopy no carbonyl groups (signal at 1690 cm$^{-1}$) could be detected and the structure of the product was confirmed by $^1$H NMR.

Example 3

PEG-tetraacrylate 2 k

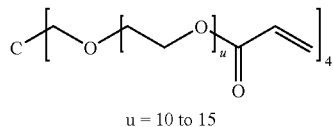

u = 10 to 15

12.7 g of 4-arm PEG 2 k ($M_n$=2323 g/mol, 21.9 meq OH) were dissolved in 250 ml of dry tetrahydrofuran under an Ar atmosphere. The solution was dried by refluxing the solvent over molecular sieves until the water content had fallen below 100 ppm, after which it was allowed to cool down to room temperature. 2.81 g of triethylamine (27.8 mmol) were added and a solution of 2.51 g of acryloylchloride (27.7 mmol) in 25 ml of dry dichloromethane was added drop wise at such a rate that the temperature of the reaction mixture remained below 30° C. The resulting suspension was filtered through ca. 1.5 cm of Celite 545, yielding a pale yellow, clear solution to which 44 mg of MEHQ were added. The solvent was removed by rotary evaporation, the remaining oil was redissolved in 150 ml of water and NaHCO$_3$ was added until pH 8. The aqueous solution was washed three times with 50 ml of diethyl ether, 15 g of NaCl were added and the product was extracted with five 50 ml portions of dichloromethane. The combined organic layers were dried with Na$_2$SO$_4$, and filtered. Removing the solvent by rotary evaporation yielded 12.9 g (93%) of a yellow oil. The structure of the product was confirmed by $^1$H NMR, which showed a degree of functionalization of ca. 95%.

Example 4

PEG-octaacrylate 2 k

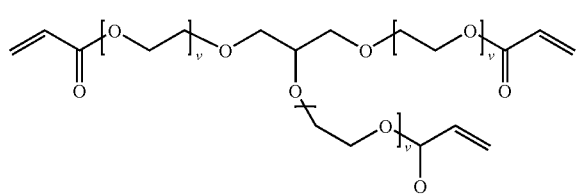

v = 3 to 8 (≈ 4.3)

Starting from 8-arm PEG 2 k ($M_n$=1985 g/mol) and following the procedure described in example 3, PEG-octaacrylate 2 k with a degree of functionalization of ca. 94% was obtained.

Example 5

PEG-tetraacrylate 15 k

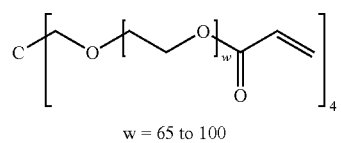

w = 65 to 100

12.08 g of 4-arm PEG 15 k ($M_n$=14861 g/mol, 3.3 meq OH) were dissolved in 150 ml of dry tetrahydrofuran under an Ar atmosphere. The solution was dried by refluxing the solvent over molecular sieves until the water content had fallen below 100 ppm, after which it was allowed to cool down to room temperature. 0.78 g of triethylamine (7.7 mmol) were added and a solution of 0.69 g of acryloylchloride (7.7 mmol) in 20 ml of dry dichloromethane was added drop wise at such a rate that the temperature of the reaction mixture remained below 30° C. The resulting suspension was filtered through ca. 1 cm of Celite 545, yielding a pale yellow, clear solution to which 44 mg of MEHQ were added. The solvent was removed by rotary evaporation, the resulting solid was redissolved in 150 ml of water and NaHCO$_3$ was added until pH 8. The aqueous solution was washed twice with 40 ml of diethyl ether, 10 g of NaCl were added and the product was extracted with four 50 ml portions of dichloromethane. The combined organic layers were dried with Na$_2$SO$_4$ and filtered. To the resulting pale yellow solution 30 mg of MEHQ were added and it was concentrated to ca. 35 ml by rotary evaporation. Precipitation in 0.8 l of cold diethyl ether and subsequent filtration and drying at 60° C. in a vacuum oven yielded 11.5 g (94%) of a white powder. The structure of the product was confirmed by $^1$H NMR, which showed a degree of functionalization of ca. 97%.

Example 6

PEG-octaacrylate 10 k

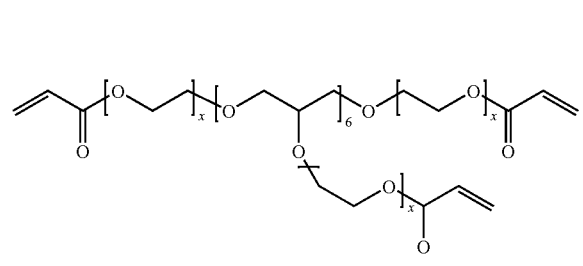

x = 20 to 30

Starting from 8-arm PEG 10 k ($M_n$=9468 g/mol) and following the procedure described in example 5, PEG-octaacrylate 10 k with a degree of functionalization between 95% and 100% was obtained.

Example 7

PEG-octaacrylate 20 k

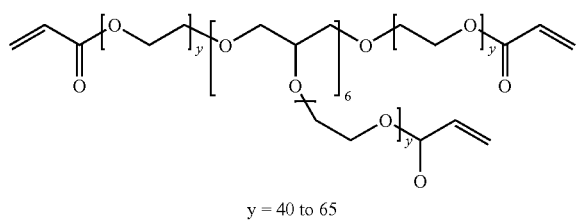

y = 40 to 65

Starting from 8-arm PEG 20 k ($M_n$=19770 g/mol) and following the procedure described in example 5, PEG-octaacrylate 20 k with a degree of functionalization between 96% and 100% was obtained.

Example 8

PEG-trisacrylate 15 k

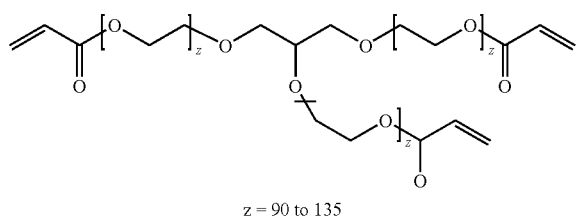

z = 90 to 135

Starting from 3-arm PEG 15 k ($M_n$=14763 g/mol) and following the procedure described in example 5, PEG-trisacrylate 15 k with a degree of functionalization of ca. 97% was obtained.

Example 9

Tris(2-[4-mercapto-butyrylamino]ethyl)amine hydrochloride

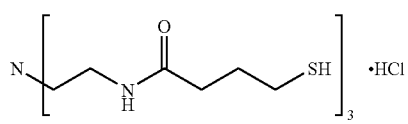

4.7 g (32 mmol) of tris(2-aminoethyl)amine and 10.3 g (101 mmol) of γ-thiobutyrolactone were dissolved in 100 ml of dry chloroform under an Ar atmosphere. The reaction mixture was stirred for 24 hours under reflux, allowed to cool to room temperature, and precipitated by slow addition of 16 ml of 2.0 M HCl in diethyl ether. After the precipitate had settled, the supernatant liquid was decanted and the precipitate was redissolved in dichloromethane, reprecipitated in diethyl ether, and dried in a vacuum oven, yielding a pale yellow, waxy material. The structure of the product was confirmed by $^1$H and $^{13}$C NMR.

Example 10

Tris(2-[2-{N-acetylamino}-4-mercapto-butyrylamino]ethyl)amine hydrochloride

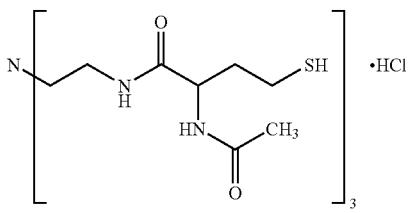

2.51 g (17.1 mmol) of tris(2-aminoethyl)amine and 8.54 g (53.7 mmol) of N-acetylhomo-cysteine thiolactone were dissolved in 50 ml of dry chloroform under an Ar atmosphere. The reaction mixture was stirred for 22 hours under reflux, allowed to cool to room temperature, and was precipitated by slow addition of 10 ml of 2.0 M HCl in diethyl ether. After the precipitate had settled, the supernatant liquid was decanted and the precipitate was redissolved in ethanol, reprecipitated in diethyl ether, and dried in a vacuum oven, yielding 10.2 g (90%) of a white powder. The structure of the product was confirmed by $^1$H and $^{13}$C NMR.

Example 11

α,ω-bis(4-mercapto-butyrylamino)-PEG 3.4 k

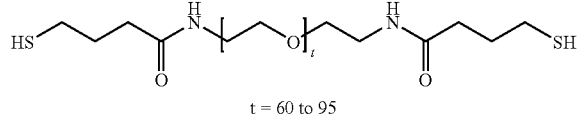

t = 60 to 95

1.27 g (32 mmol) of α,ω-bisamino-PEG ($M_n$=3457 g/mol, 0.72 meq amine), 0.22 g (2.1 mmol) of γ-thiobutyrolactone, and 20 mg of 4-(dimethylamino)-pyridine were dissolved in 10 ml of dry dichloromethane under an Ar atmosphere. The reaction mixture was heated to reflux and stirred for 32 hours, after which the product was isolated by precipitating twice in cold diethyl ether and dried in a vacuum oven, yielding 1.23 g (91%) of white powder. The structure of the product was confirmed by $^1$H NMR.

Gelation

Example 12

7.0 mg (4.0 μeq thiol) of the product from example 2 and 20.0 mg (4.0 μeq acrylate) of the product from example 8 were each dissolved in equal amounts of an aqueous 0.30 M triethanolamine/HCl buffer at pH 8.0. Both solutions were cooled to 0° C., quickly mixed and placed between the plates of a parallel plate rheometer. The plates were kept at 37° C. and the storage (G') and loss (G") moduli were measured as a function of time at a frequency of 10 Hz. The gel point, defined as the crossover point of G' and G", was determined for several PEG concentrations (table 1).

TABLE 1

| PEG (wt %) | Gel point (s) | G' at 30 min (kPa) |
|---|---|---|
| 9.2 | 632 | 2.9 |
| 10.8 | 486 | 4.3 |
| 12.3 | 316 | 8.4 |
| 14.9 | 289 | 9.6 |

Example 13

41.9 mg (64.0 µeq thiol) of the product from example 1 and 40.3 mg (63.5 µeq acrylate) of the product from example 3 were each dissolved in 237 mg of an aqueous 0.050 M triethanolamine/HCl buffer at pH 7.6. Both solutions were cooled to 0° C., quickly mixed and placed between the plates of a parallel plate rheometer. The plates were kept at 37° C. and the storage (G') and loss (G") moduli were measured as a function of time at a frequency of 10 Hz. The gel point, defined as the crossover point of G' and G", was determined (table 2).

TABLE 2

| PEG (wt %) | Gel point (s) | G' at 10 min (kPa) |
|---|---|---|
| 14.8 | 76 | 83.0 |

In Vitro Degradation

Example 14

155.8 mg (238 µeq thiol) of the product from example 1 and 150.6 mg (237 µeq acrylate) of the product from example 3 were each dissolved in 0.59 g of an aqueous 0.030 M triethanolamine/HCl buffer at pH 7.4. Both solutions were cooled to 0° C., quickly mixed and cylindrical gels (70 µl) were cast in Teflon molds (diameter 6 mm). The gels were cured for 1 hr at 37° C. and placed in 10 mM PBS (pH 7.4) at 37° C. Swelling due to hydrolysis of the ester linkages was monitored by weighing the gels at regular intervals (FIG. 1: average values of 6 samples; the line shows a logarithmic curve fit). The gel was completely dissolved after ca. 64 days.

Example 15

Several different combinations of thiol and acrylate compounds were gelled, following the procedure described in example 14. The times after which the gels were completely dissolved are listed in table 3.

TABLE 3

| | Thiol | | | Acrylate | | | |
|---|---|---|---|---|---|---|---|
| Exp. # | ex. # | chains | chain length (g/mol) | ex. # | chains | chain length (g/mol) | Days to complete dissolution |
| 15a* | 2 | 2 | 1740 | 8 | 3 | 4980 | 11 |
| 15b | 1 | 4 | 655 | 3 | 4 | 635 | 64 |
| 15c | 1 | 4 | 655 | 6 | 8 | 1240 | 73 |
| 15d | 1 | 4 | 655 | 4 | 8 | 302 | 121 |
| 15e | 1 | 4 | 655 | 4 | 8 | 302 | 157 |

*comparative example

Example 16

Cell Occlusivity

Methods

Dry, highly porous sponges of polyvinylalcohol (PVA) were cut into cylinders, 3 mm in diameter and 5 mm tall, and were sterilized by swelling and subsequent autoclaving in deionized water. The resulting sterile cylindrical sponges were then lyophilized to remove excess water and stored sterile until needed further.

A standard fibrin glue kit was diluted such that the final concentration of the fibrinogen component was four fold lower and the final concentration of the thrombin component was 125 fold lower than that for a standard kit. Equal volumes of the fibrinogen and thrombin solutions were mixed and adsorbed into the PVA sponge, creating a fibrin network amongst the pores of the PVA.

The thus formed fibrin-PVA sponges were stored in sterile Petri dishes until implantation in the animal (+control) or entrapment in a membrane material.

Membrane PEG gels were cast at room temperature under sterile conditions in cylindrical stainless steel molds (Ø7 mm, height 7 mm), using membrane kits containing equimolar amounts of 4-arm PEG-thiol 2 k and 8-arm PEG-acrylate 2 k as well as a triethanolamine/HCl buffer with CMC as viscosity modifier. Before gelation set in, a fibrin sponge was placed in the center of each membrane gel. The molds were covered and gels were allowed to cure for ca. 1 hour, after which they were transferred to sterile 10 mM PBS and stored in an incubator at 37° C. overnight.

In a standard operation procedure, fourteen adult female rats received each four implants randomly distributed over four dorsal subcutaneous pockets. In three of the pockets a membrane implant was placed and in the fourth pocket two sponges filled with fibrin were placed as positive control. The incisions were closed by staples. Animals were sacrificed after several time points post-operatively and the implants were fixed in 4% PFA/PBS. Dehydration series with 70, 90 and 100% EtOH were accomplished while slowly shaking at RT. Each dehydration step lasted 24 h in which the solution was exchanged once. After dehydration the explants were infiltrated for 36 h by freshly catalyzed Histocryl solution, which was exchanged twice during the infiltration. Every sample was then embedded in a gelatin capsule (EMS, size 13) with freshly catalyzed Histocryl solution. The embedded explants were sectioned on a Rotary Microtom (MICROM) with a knife (d shaped, MICROM). Sections were stained with Meyer's hematoxylin (Merck) and an aqueous eosin solution (1%, Sigma), mounted in Mowiol.

The degree of cell invasion into fibrin filled PVA sponges was quantified by counting DAPI stained cell nuclei in 36 to 45 histological sections (4 µm thick) of tissue explants by automated image analysis.

Results

After 1 month PEG shielded implants were basically cell free whereas in unshielded implants the fibrin phase of the sponge was complete invaded by densely packed cells. Statistical analysis showed highly significant differences (P=0.00004) between samples and positive controls. At the following time points, essentially no changes in the number of cells found in the positive controls were observed. The average value (±SD) for the control samples was $(1.3\pm0.3)\cdot10^6$ cells per mm$^3$ (n=12).

Figure 2:
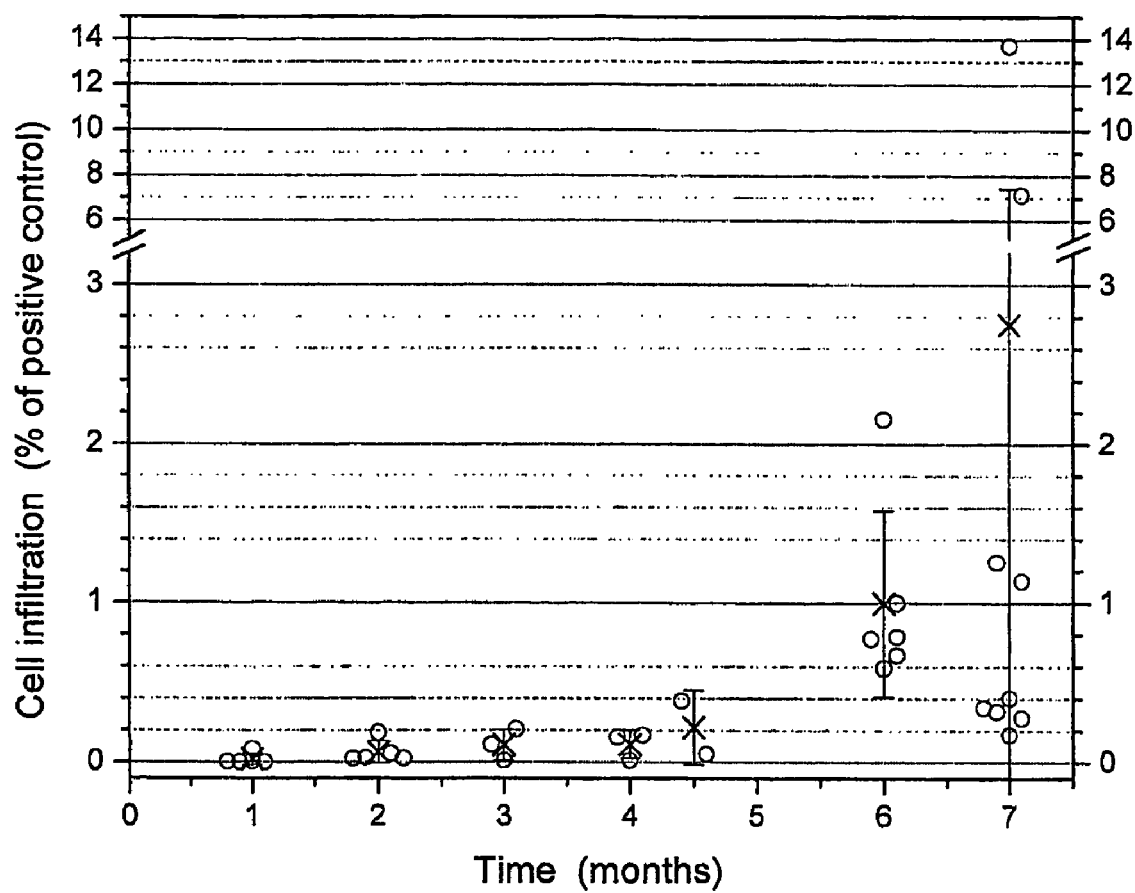

FIG. 2 shows the number of cells found in each PEG shielded sponge as a percentage of the average number in the control samples (open circles). The average percentages for each time point (±SD) are indicated with crosses. Between 1 and 4 months the number of cells found in the samples increased only slightly. Although a clear increase in cell infiltration was observed after 6 months, in most of the sponges the number of cells was still below 1% of that in the positive control. After 7 months, the PEG membranes were mostly disintegrated and the number of cells had increased to (2.8±4.7)% of that in the positive control. The strong variation between individual samples at this time point may be explained by slight variations in the time to full degradation between the individual PEG membranes. When "cell occlusive" is defined as allowing less than 1% cells to infiltrate, it can be concluded that the membrane is cell occlusive for ca. 6 months.

The invention claimed is:

1. Kit for preparing a cell-occlusive membrane, comprising
   a first precursor A comprising a core carrying n chains each having a conjugated unsaturated group or a conjugated unsaturated bond attached to any of the last 20 atoms of the chain and
   a second precursor B comprising a core carrying m chains each having a thiol group attached to any of the last 20 atoms of the chain,
   wherein
   m is greater than or equal to 2,
   n is greater than or equal to 2, and
   m+n is greater than or equal 5, and
   each core of the precursors forms a crosslinking-point if m and n are greater than 2, and
   if m is equal to 2 the corresponding crosslinking-point corresponds to the core of the adjacent first precursor A, and
   if n is equal to 2 the crosslinking-point corresponds to the core of the adjacent second precursor B, and
   the adjacent crosslinking-points are connected by a chain having less than 600 atoms,
   wherein the first precursor A and the second precursor B are separated from each other; and
   wherein the first precursor is selected from the group consisting of:

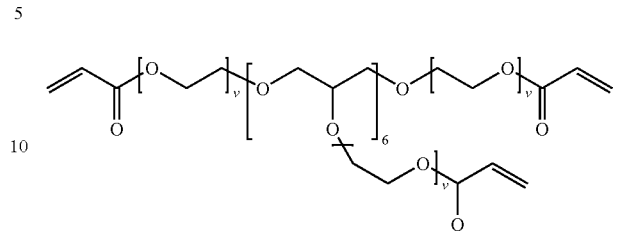

where v=3 to 8.

2. Kit according to claim 1 additionally comprising a buffered aqueous solution and/or a viscosity modifier.

3. Kit according to claim 1, wherein the second precursor is selected from the group consisting of:

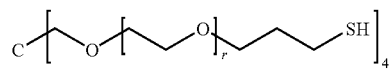

where r=7 to 15.

4. A compound comprising:

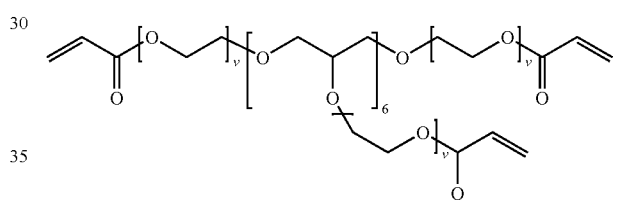

where v=3 to 8.

5. A compound comprising:

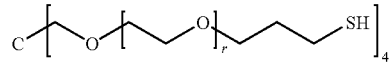

where r=7 to 15.

* * * * *